United States Patent [19]

Honma

[11] 4,317,113
[45] Feb. 23, 1982

[54] PHOTOELECTRIC SMOKE SENSOR
[75] Inventor: Hiroshi Honma, Hino, Japan
[73] Assignee: Hochiki Corporation, Tokyo, Japan
[21] Appl. No.: 177,250
[22] Filed: Aug. 11, 1980
[30] Foreign Application Priority Data
Aug. 24, 1979 [JP] Japan .................................. 54/107981
[51] Int. Cl.³ ............................................. G08B 17/10
[52] U.S. Cl. .................................. 340/630; 250/565;
250/573; 356/438
[58] Field of Search ................. 340/628, 630; 250/573,
250/574, 575, 576, 577, 564, 565; 356/438, 439

[56] References Cited
U.S. PATENT DOCUMENTS

| | | | |
|---|---|---|---|
| 3,872,315 | 3/1975 | Boll | 356/439 |
| 3,982,130 | 9/1976 | Trumble | 340/630 |
| 3,988,590 | 10/1976 | Johnson | 250/565 X |
| 3,992,109 | 11/1976 | Bock | 250/565 X |
| 4,017,193 | 4/1977 | Loiterman | 340/630 X |
| 4,035,087 | 7/1977 | Mori et al. | 250/565 |
| 4,047,819 | 9/1977 | Goldberg | 250/565 X |
| 4,084,906 | 4/1978 | Bibbero | 250/565 X |
| 4,093,867 | 6/1978 | Shah et al. | 356/438 X |
| 4,128,339 | 12/1978 | Yamazaki et al. | 250/565 X |
| 4,203,100 | 5/1980 | Yamauchi et al. | 250/573 X |

FOREIGN PATENT DOCUMENTS 52-37084 3/1977 Japan .................................. 340/630

Primary Examiner—John W. Caldwell, Sr.
Assistant Examiner—Daniel Myer
Attorney, Agent, or Firm—Phillips, Moore, Weissenberger, Lempio & Majestic

[57] ABSTRACT

In a photoelectric smoke sensor which produces a fire alarm signal when an amount of attenuation of received light exceeds a predetermined level due to smoke flowing into a space between light emitting and light receiving devices, the level of a receiving light signal from the light receiving device is converted by a converting level control signal. An initial value of the receiving light signal is converted into a digital quantity which is stored in a memory circuit. The digital content of the memory circuit is then converted into an analog quantity. The analog quantity is then compared with the level-converted receiving signal to produce a fire alarm signal. The analog quantity and the level-converted receiving signal are compared with each other at a predetermined period to correct the converting level control signal when there is a difference between the analog quantity and the level-converted receiving signal as a result of the comparison. With such a scheme, a change of an amount of received light due to dust or dirt of an optical system of the smoke sensor is automatically corrected. When the level correction reaches a limit, an alarm is issued for inspection and maintenance of the sensor.

8 Claims, 13 Drawing Figures

PHOTOELECTRIC SMOKE SENSOR

BACKGROUND OF THE INVENTION

The present invention relates to a photoelectric smoke sensor for detecting a fire from a reduction in the amount of received light caused by smoke flowing into a space between a light emitting device and a light receiving device.

In a photoelectric smoke sensor having a construction in which a light emitting device and a light receiving device are separately disposed, an optical system can be accumulatively coated with dust, and can be stained and soiled through its long use. Also, the light emitting and receiving elements associated with the optical system necessarily age. These factors mainly reduce the amount of light in the optical system to often cause a false alarm.

Attempts have been made to compensate for the attenuation of the received light caused by factors other than smoke. In Japanese Laid-open patent application Nos. 16,481/74 and 37,084/77, and in Japanese patent application Publication No. 37,789/77, fire detection is made by comparing light receiving signals stored in an analog or digital manner in a memory with receiving light signals received periodically. At the same time, a change in the amount of the received light, caused by dust and dirt or soil attached to the optical system, is detected at given intervals of time, thereby compensating for the stored amount of receiving signals.

The proposal is effective and useful as long as a lower correction is required. As mentioned above, the proposal corrects the memory contents as a reference of comparison so as to follow an amount of attenuation of the light due to the dust and soil attached to the optical system and compares the corrected signal with a light amount measured at a present time. Therefore, as the dust or soil of the optical system increases, the received light per se at the present time becomes small, so that the S/N ratio in the case of signal processing deteriorates. In this system, the memory content is corrected to the receiving light signal at the present time at a predetermined period of time. Accordingly, the memory content itself contains a receiving light signal under a worse S/N ratio condition. As a result, the receiving light signal at the present time having a worse S/N ratio is compared with the memory content having a worse ratio, so that compensation accuracy increases as the dust or soil of the optical system increases. Therefore, a possible range of the compensation of the memory contents has a certain limit. In this proposal, the memory contents immediately after the smoke sensor is installed is corrected with the progression of the aging of the optical system. When an inspection of the smoke sensor is required, it is impossible to know what amount of correction has been made or if the correction is within a proper correcting range or not. In the worst case, accordingly, there is a problem that a false alarm or non-fire alarm is issued.

In addition, this system automatically performs the correction and storage of the memory content, which is automatically corrected at a predetermined period. Accordingly, if smoke has occurred due to a fire at the time that the above-mentioned correction and storage operation is performed, and thus the smoke detector is going to issue an alarm, then the condition where the smoke exists is stored as a memory content for a reference of comparison. Therefore, there is the possibility of the occurrence of a situation where a smoke detector fails to perform its normal operations. Thus this system is not reliable.

There has been another proposal, as disclosed in a Japanese Laid-open patent application Nos. 56,981/77 and 93,699/77, to compensate for the attenuation of the received light. This proposal successively stores the receiving light signal into a shift register and compares the received light amount at the final state of the shift register with the present amount of the received light for the fire detection. Because of the use of the shift register, however, the fire sensor does not function as a sensor from the time that power is turned on until the receiving light signal reaches the final stage of the shift register. Therefore, a long time is taken for a sensitivity test immediately after the sensor is installed.

SUMMARY OF THE INVENTION

Accordingly, an object of the present invention is to provide a highly reliable photoelectric smoke sensor which surely compensates for a change of the received light amount due to dust and dirt which accumulates on the optical system, so that the photoelectric smoke sensor stably operates with a minimized adverse effect caused by dust and dirt of the optical system.

Another object of the present invention is to provide a photoelectric smoke sensor with reliable and easy maintenance and inspection in which when the compensation for the change of the received light amount has reached a limit, an alarm representing the limit state is issued exteriorly.

Yet another object of the present invention is to provide an inexpensive and reliable photoelectric smoke sensor with a simplified circuit construction for digital and analog conversions for detecting a fire and for correcting the level of a receiving light signal by storing a receiving light signal at an initial condition in the form of digital signal and then by converting a digital value which represents the initial receiving light signal into a corresponding analog quantity.

According to one aspect of the present invention, there is provided a photoelectric smoke sensor which produces a fire alarm signal when an amount of attenuation of received light exceeds a predetermined level due to smoke of a fire flowing into a space between light emitting and light receiving devices, comprising: a signal level converting circuit for varying a level of a receiving light from the light receiving device in accordance with a converting level control signal; a memory circuit for storing in digital form an initial value of the receiving light signal from the signal level converting circuit in; a D/A converting circuit for converting the digitally stored contents of the memory circuit into an analog quantity; a first comparing circuit which compares the analog output signal from the D/A converting circuit with the output signal from the signal level converting circuit to produce the fire alarm signal when there is a difference between both of the output signals; a second comparing circuit which compares the analog output signal from the D/A converter with the output signal from the signal level converting circuit at a predetermined period and produces a comparison output signal when there is a level difference between both of these output signals; and a converted level correcting circuit which produces the converting level control signal for correcting a converting level in the signal level converting circuit when the second comparing circuit produces the comparison output signal.

According to another aspect of the present invention, there is provided a photoelectric smoke sensor, which produces a fire signal when an amount of light attenuation exceeds a given level due to smoke flowing between light emitting and light receiving devices, comprising: a signal level converting circuit for varying a level of a receiving light signal from the light receiving device in accordance with a converting level control signal; a first memory circuit for storing an initial value of the receiving light signal from the signal level converting circuit; a second memory circuit for storing periodically or updating the receiving light signal from the signal level converting circuit at a first predetermined period; a comparing circuit which compares the stored receiving light signals respectively stored in the first and second memory circuits with each other to produce a comparison output signal when there is a level difference between the stored receiving light signals in the first and second memory circuits; a converting level correcting circuit for producing the converting level control signal to correct a converting level in the signal level converting circuit when the comparing circuit produces the comparison output signal; and a clock circuit for generating a clock signal which controls the converting level correcting circuit to perform the correcting operation thereof at a second predetermined period which is longer than the first predetermined period of the second memory circuit.

A preferred embodiment of the smoke sensor according to the invention futher comprises means for producing an alarm signal for maintenance and inspection when the level correcting operation in the converting level correcting circuit reaches a limit.

Preferably, the signal level converting circuit may have a variable gain amplifier for receiving the receiving light signal, of which the gain is changed by the converting level control signal from the converting level correcting circuit.

The signal level converting circuit may have an attenuator and analog switches, in such a way that the analog switches are controlled by the converting level control signal to change an amount of the attenuation of the attenuator.

The above and other objects and features of the present invention will be apparent from the following description taken in connection with the accompanying drawings, in which;

DETAILED DESCRIPTION OF PREFERRED EMBODIMENTS

Figure 1:
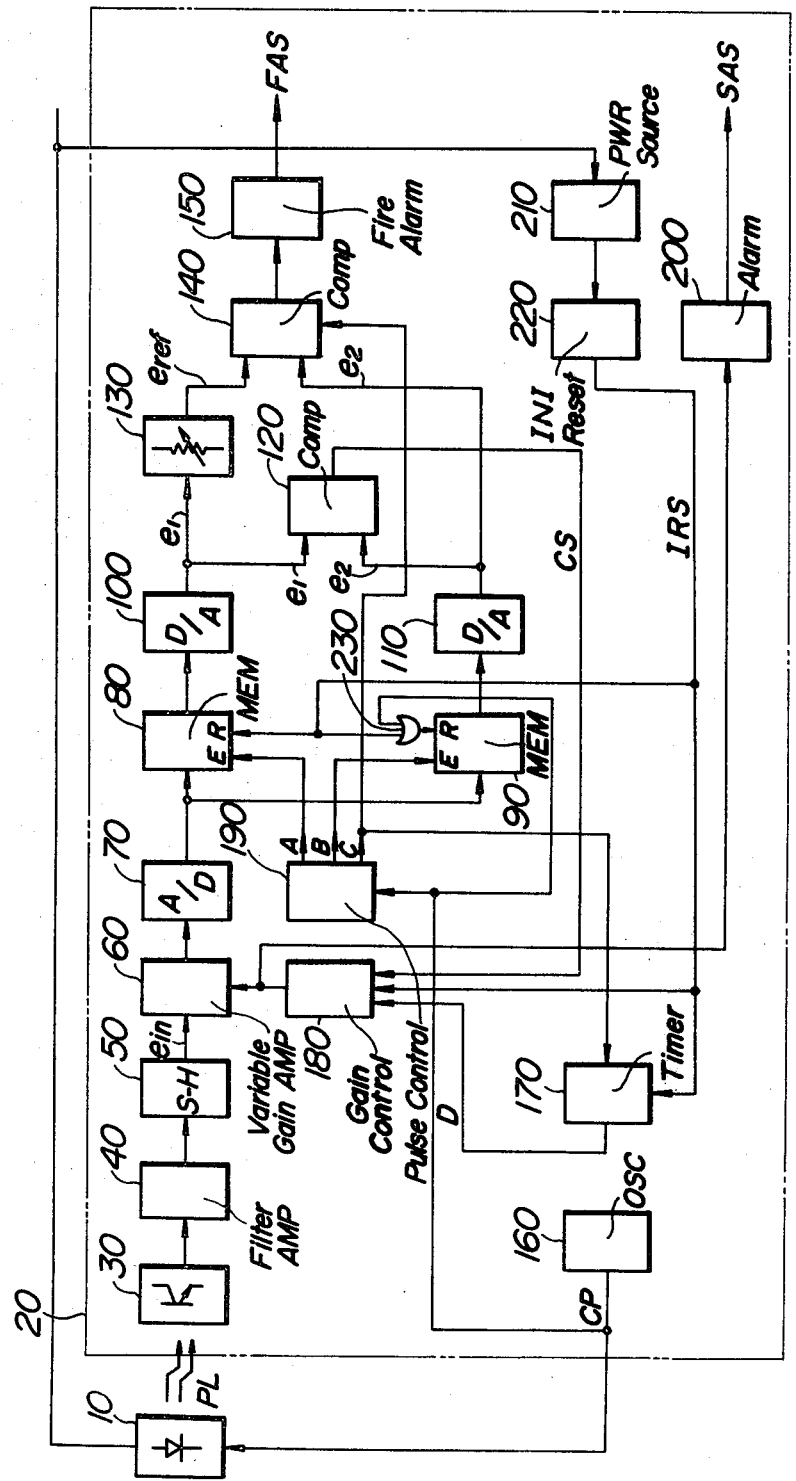
FIG. 1 is a block diagram showing an embodiment of a photoelectric smoke sensor according to the present invention.

FIG. 1 shows a block diagram of an embodiment of a photoelectric smoke sensor according to the present invention. In FIG. 1, reference numeral 10 designates a light emitting device including a light emitting diode for emitting pulsive light PL at a predetermined period and reference numeral 20 designates a light receiving device disposed opposite to and separated from the light emitting device 10 by a given distance.

Figure 2:
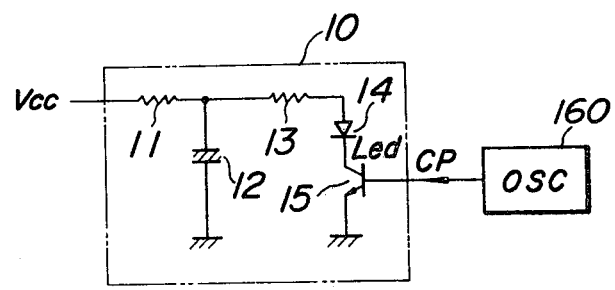
FIG. 2 is a circuit diagram showing an embodiment of a light emitting device shown in FIG. 1

The light emitting device 10 may be arranged, for example, as shown in FIG. 2. In FIG. 2, the light emitting device 10 has a capacitor 12 connected via a resistor 11 to a power supply source Vcc, a resistor 13 connected to the capacitor 12, a light emitting diode 14, and a control transistor 15. In this circuit arrangement, the other terminal of the capacitor 12 and the emitter of the transistor 15 are connected to ground. To the base of the transistor 15 is applied an oscillating output from an oscillator 160 which will be described later. The light emitting diode 14 is driven in accordance with the oscillating output.

Further, a control circuit for controlling a light emitting signal may be provided between the oscillating circuit 160 and the base of the transistor 15. This light emitting signal control circuit may be formed, for example, by a conventional monostable multivibrator producing its output signal only for a predetermined period of time, or by a conventional gate control type oscillating circuit which oscillates at a fixed frequency only for a predetermined time duration. In the case of the monostable multivibrator, the driving time of the light emitting diode can be shortened, so that the current consumed in a smoke detector can be reduced. On the other hand, in the case of the gate control type oscillating circuit, the light emitting diode 14 is driven at a fixed frequency for a predetermined time duration, so that this oscillating circuit is effectively employed in order to eliminate disturbing light and noise in the light receiving device.

In the light receiving device 20, reference numeral 30 designates a photosensitive element such as a photodiode, phototransistor or the like for converting the received light into an electrical signal or a receiving light signal; 40 designates a filter amplifier of an active filter type which removes disturbing light and noise components contained in the receiving light signal from the light receiving element 30 and amplifies the noise-free receiving light signal; 50 designates a conventional peak value holding circuit which samples the amplified receiving light signal at a predetermined time and holds the sampled signal; 60 designates a signal level converting circuit which converts the level of the receiving light signal $e_{in}$ from the peak value holding circuit 50; for example, 60 is a variable gain amplifier circuit for amplifying with a set gain the receiving light signal $e_{in}$ from the circuit 50; 70 designates an analog to digital (A/D) converter for converting the output signal from the variable gain amplifier circuit 60 into a digital signal; for example, 70 is a voltage/frequency converter such as model LM131 manufactured by National Semiconductor Inc.; 80 designates a first memory circuit which receives a digital signal from the A/D converter 70 and stores the digital value of the receiving light signal initially inputted; 90 designates a second memory circuit which receives the digital signal from the A/D converter 70 to store the digital value of the receiving light signal and to refresh or update a stored signal at a predetermined period. The first and second memory circuits 80 and 90 may be constructed of BCD counters which receive at respective enable terminals pulse signals A and B (see FIG. 8) from a pulse control circuit 190 which will be described later. Reference numerals 100 and 110 designate digital to analog (D/A) converters for converting the memory output signals from the first and second memory circuits 80 and 90 into analog signals; for example, 100 and 110 are model LM1508 manufactured by National Semiconductor Inc.; 120 designates a first comparator having a conventional circuit arrangement for comparing the analog output signals from the D/A converters 100 and 110 to produce a comparison output; 130 designates a sensitivity setting circuit, for example, a variable resistor VR1 as shown in FIG. 3, for setting a reference signal level sensitivity setting circuit 130 is used for determining if there is a fire from an initial value of the receiving light signal stored and held in the first memory circuit 80; 140 designates a second comparing circuit for determining if there is a fire on the basis of the reference signal obtained from the sensitivity setting circuit 130; 150 designates a fire alarm signal generating circuit, for example, a fire alarm output circuit formed by a relay, thyristor or transistor which is driven by the fire detection output from the comparing circuit 140 to produce a fire alarm signal FAS.

Reference numeral 160 is a conventional oscillating circuit for producing an oscillating pulse CP; 170 designates a clock circuit having a counter for counting the number of pulse signals C from the pulse control circuit 190, and for producing pulse signals D which determine a gain correcting timing of the variable gain amplifier 60 at a predetermined period, for example, at every 10 hours; 180 designates a gain control circuit for controlling the setting of the gain of the variable gain amplifier 60; as previously mentioned, 190 a pulse control circuit which has a gate control type pulse generator, driven by the oscillating pulse CP from the oscillating circuit 160, for providing operation timings of the first and second memory circuits 80 and 90, the second comparing circuit 140 and the clock circuit 170 by the output pulses from the pulse generator; 200 designates an alarm circuit which produces an alarm signal for maintenance and inspection when a detection is made that the set gain of the gain control circuit 180 has reached a limit, and may be, for example, a driving circuit for an alarm display in the form of a relay, a thyristor or a transistor amplifier; 210 designates a power source circuit of the light receiving device 20; 220 designates an initial reset circuit to which the output signal from the power source circuit 210 is applied to produce an initial reset signal IRS in response to the power-on operation of the power source circuit 210; and 230 is an OR gate for receiving the oscillating pulse CP from the oscillating circuit 160 and the initial reset signal IRs from the initial reset circuit 220 and for producing an OR output signal which is applied to the reset terminal of the memory circuit 90.

Figure 3:
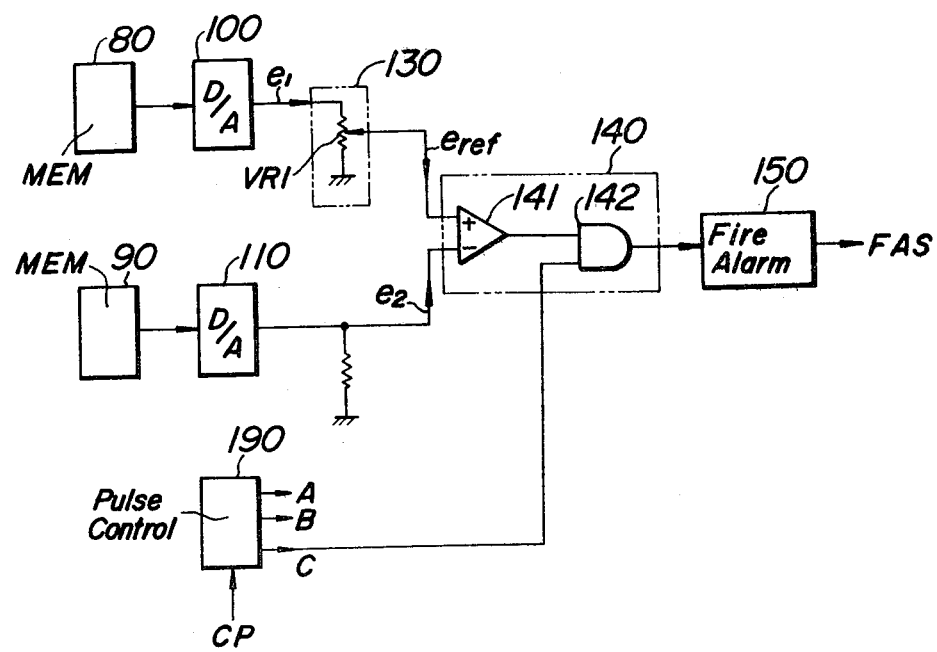
FIG. 3 is a block diagram showing embodiments of a sensitivity setting circuit and a comparing circuit shown in FIG. 1.

A detailed construction of the comparing circuit 140, together with the sensitivity setting circuit 130, is illustrated in FIG. 3. As shown, an initial value $e_1$ of the receiving light signal from the D/A converter 100 is voltage-divided into a given level by the variable resistor VR1 of the sensitivity setting circuit 130, which in turn is applied as a reference signal $e_{ref}$ to the positive polarity input terminal of a conventional comparator 141 of the comparing circuit 140. The output signal $e_2$ from the D/A converter 110 is applied to the negative input terminal of the comparator 141. The output signal from the comparator 141 and the pulse signal C from the pulse control circuit 190 are supplied to an AND gate 142, whose output signal is applied as the output from the comparing circuit 140 to the fire alarm signal generating circuit 150.

Figure 4:
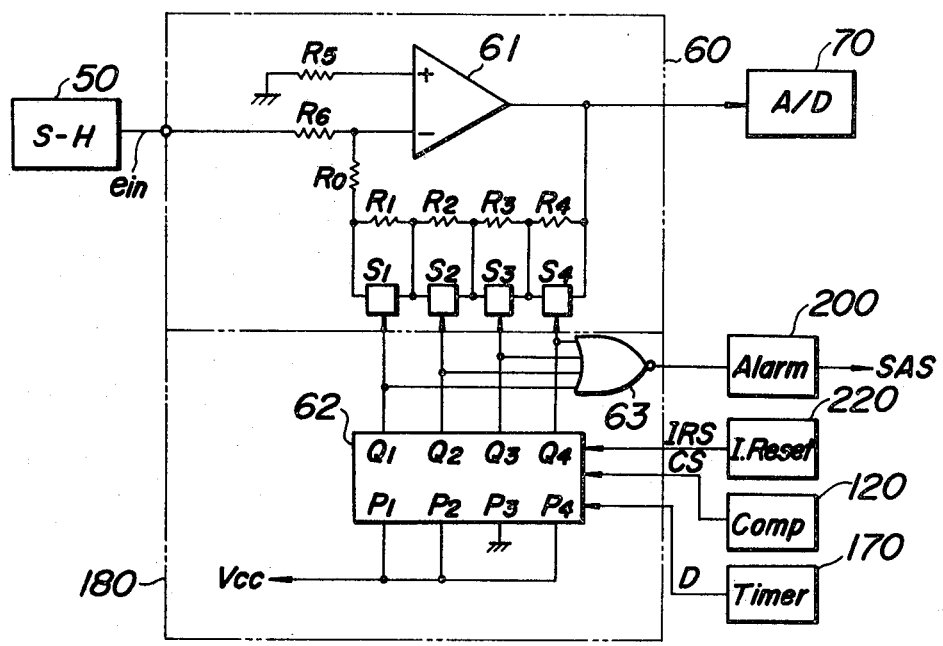
FIGS. 4 and 5 are circuit diagrams showing respectively embodiments of a signal level converting circuit and a converting level correcting circuit.

FIG. 4 shows embodiments of a signal level converting circuit having the gain control circuit 180 and the variable gain amplifier circuit 60. An amplifier 61, having feedback resistors R0 to R4 and input resistors R5 and R6, receives the receiving light signal $e_{in}$ from the sample/hold circuit 50, via the resistor R6. Reference numeral 62 designates a preset type up/down counter for producing four-bit binary signals Q1 to Q4. S1 to S4 are analog switches for selectively shortcircuiting the feedback resistors R1 to R4 in accordance with the output signal from the up/down counter 62. A NOR gate 63 applies a high (H) level output to the alarm circuit 200 when the output bits from the up/down counter 62 are all at low (L) level. For example, model CD 4066 manufactured by the Radio Corporation of America (RCA) may be used for the analog switches S1 to S4. In this circuit arrangement, the gain G of the amplifier 61 may be changed by selectively shortcircuiting the feedback resistors R1 to R4 by means of the analog switches S1 to S4. In this case, the maximum gain Gmax is given by Gmax=(R0+R1+R2+R3+R4)/R6 and the minimum gain Gmin is expressed by Gmin=R0/R6.

In operation, when the power source circuit 210 is turned on, the initial reset signal IRS is applied from the initial reset circuit 220 to the up/down counter 62, the power source voltage Vcc is applied to the preset terminals P1, P2 and P4 and ground potential is applied to the preset terminal P3 to preset the outputs Q1 to Q4. Upon the application of these preset signals, the up/down counter 62 produces binary outputs (Q1, Q2, Q3, Q4)=(1101) where only the output Q3 is at the L level. At this time, the outputs Q1, Q2 and Q4 having the H level turn on the analog switches S1, S2 and S4, so that a resistance of the feedback resistors is given by (R0+R3).

Assuming that the input resistor R6=100 KΩ, and the feedback resistors R0=96 KΩ, R1=1 KΩ, R2=2 KΩ, R3=4 KΩ, and R4=8 KΩ, the gain G1 is $$G1=(R0+R3)/R6=100 \text{ K}\Omega/100 \text{ K}\Omega=1.0.$$

The up/down counter 62 performs an up count or down count depending on the output CS from the first comparator circuit 120. As seen from the embodiment shown in FIG. 1, the comparator 120 compares the output signals $e_1$ and $e_2$ from the D/A converters 100 and 110. When $e_1 > e_2$, the output CS of the comparator 120 has the output signal CS of the L level to control the up/down counter 62 to count downwardly. When $e_1 < e_2$, it produces an H level output to control the up/down counter 62 to count upwardly.

Accordingly, for example, at an instant t2 after 10 hours from turning on the power (see FIG. 8), the clock circuit 170 produces a pulse signal D. At this time, the output CS of the comparator circuit 120 is at the L level. Therefore, the up/down counter 62 counts downwardly by 1 bit, so that the binary outputs Q1 to Q4 are counted downwardly from "1101" to "0101". As a result, the analog switches S1 and S3 are turned off while the analog switches S2 and S4 are turned on. The gain G2 at this time is $$G2 = (R0 + R1 + R3)/R6 = 101 \text{ K}\Omega/100 \text{ K}\Omega = 1.01.$$

The equation shows that the amplification gain of the receiving light signal is increased by 1% from the initial value. The gain control is performed by the output signal D obtained from the clock circuit 170 in synchronism with the pulse signal C of the pulse control circuit 190. Since the second memory circuit 90 does not receive the pulse signal C, the second memory circuit 90 is under a holding condition at this time. As a consequence, the output $e_2$ of the D/A converter 110 is never changed in accordance with the change of the gain.

The relation $e_1 > e_2$ is obtained not only by the light attenuation due to dirt of the optical system but also by the smoke flow in case of a fire. At this time, if the clock circuit 170 produces the pulse signal D, the above-mentioned gain control is performed. However, an amount of the gain change at one time of the gain control is extremely small, e.g. 1% and such gain change occurs very slowly, i.e., once for each 10 hours. This means that the smoke sensor never fails to detect the level reduction of the receiving light signal in case of a fire due to increasing the gain at that time.

Furthermore, when the compensation of the receiving light signal with respect to dirt or the like of the optical system is continued for a long time, the binary outputs Q1 to Q4 of the up/down counter 62 become "0000" to turn off all the analog switches S1 to S4, so that the maximum gain Gmax is attained. As a result, it is impossible to compensate for the subsequent light attenuation. To avoid this situation, a fail-safe function is provided in which when the binary outputs become "0000", the output from the NOR gate 63 becomes the H level to drive the alarm circuit 200 thereby to issue an alarm signal notifying that the gain control has reached a limit.

In the embodiment shown in FIG. 4, the gain in the smoke sensor may be changed or switched over 16 steps ranging from the minimum gain to the maximum gain. In connection with the compensation for a longer period of time, a range of the gain change may be further expanded by additionally increasing the number of the feedback resistors R0 to R4, the analog switches S1 to S4, and the output bits of the up/down counter 62 by 4 bits, for example. Further, a scale for the compensation may be made finer up to 0.1%, for example, in terms of a rate of the light attenuation per one step.

With such a circuit construction, even when the amount of the light incident upon the light receiving element 30 is reduced by the dust or dirt of the optical system, the level of the receiving light signal for the judgement of an occurrence of a fire is corrected to be comparable with that of the receiving light signal at the initial stage when the optical system is not soiled or stained, so far as it is possible to control the gain effectively.

Figure 5:
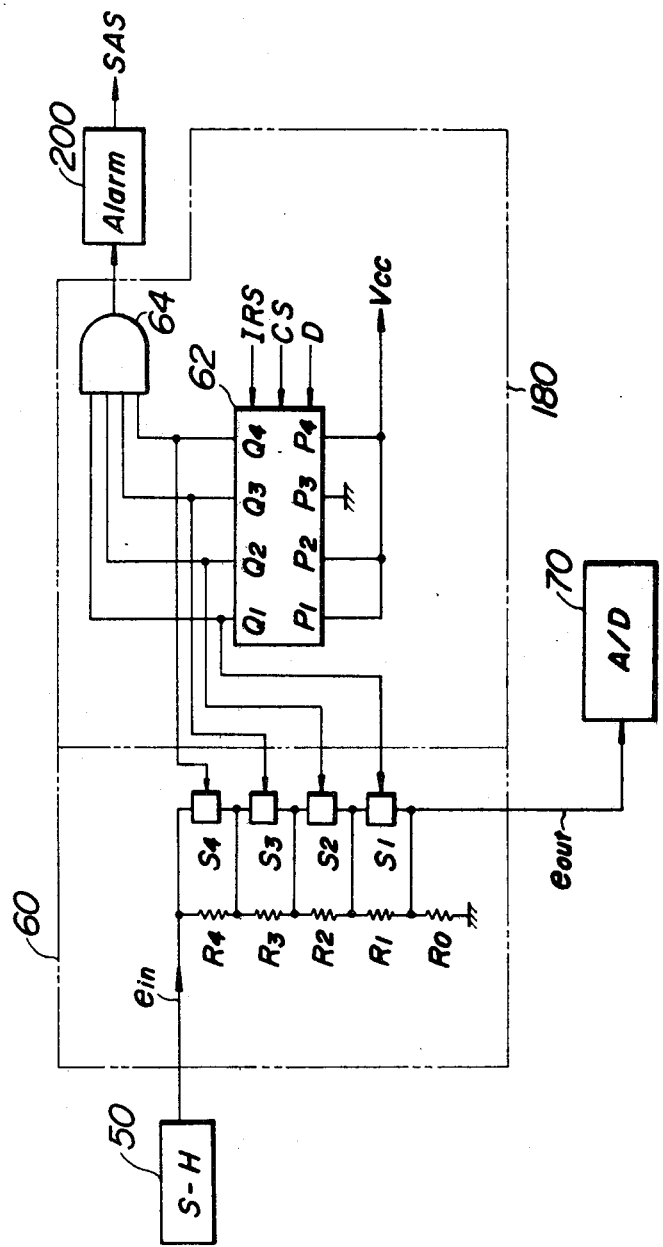

FIG. 5 shows another embodiment of the signal level converting circuit which provides an operation equivalent to that of the gain control means shown in FIG. 4. The signal level converting circuit of this embodiment controls the amount of the attenuation of the receiving light signal $e_{in}$ instead of controlling the gain of the amplifier 61.

In this embodiment, the respective analog switches S1 to S4 are connected so as to selectively shortcircuit the resistors R1 to R4 of those voltage-dividing resistors R0 to R4 which are connected in series. The analog switches S1 to S4 are switched to the ON or OFF state by binary outputs Q1 to Q4 of the up/down counter 62. Specifically, when all of the analog switches S1 to S4 are ON, the receiving input signal $e_{in}$ is transferred to an output signal $e_{out}$ with no attenuation. When all of the analog switches S1 to S4 are OFF, the output signal $e_{out}$ is given by $$e_{out} = \{R0/(R0 + R1 + R2 + R3 + R4)\} \times e_{in}.$$

As seen from the above equation, the amount of the attenuation of the receiving light signal $e_{in}$ is at the maximum under this condition. Therefore, the amount of the attenuation is switched from a high amount to a low amount so as to compensate for the decrease of the level of the receiving light signal due to the dust or dirt of the optical system. In this way, the level of the receiving light signal is always to be substantially equal to the level of the receiving light signal immediately after the power is turned on.

The respective outputs Q1 to Q4 of the up/down counter 62 may be supplied to an AND gate 64 and when the level conversion has reached a limit, the AND gate 64 detects the limit state of the level attenuation, thereby issuing an alarm signal SAS for maintenance and inspection from the alarm circuit 200.

When the change of the gain (FIG. 4) or the attenuation (FIG. 5) has reached the limit to issue an alarm for maintenance and inspection, it is necessary to clean the optical system and to turn on the power source again. As a result, the smoke sensor is placed in an initial reset condition and the operation as mentioned above is repeated.

Figure 6:
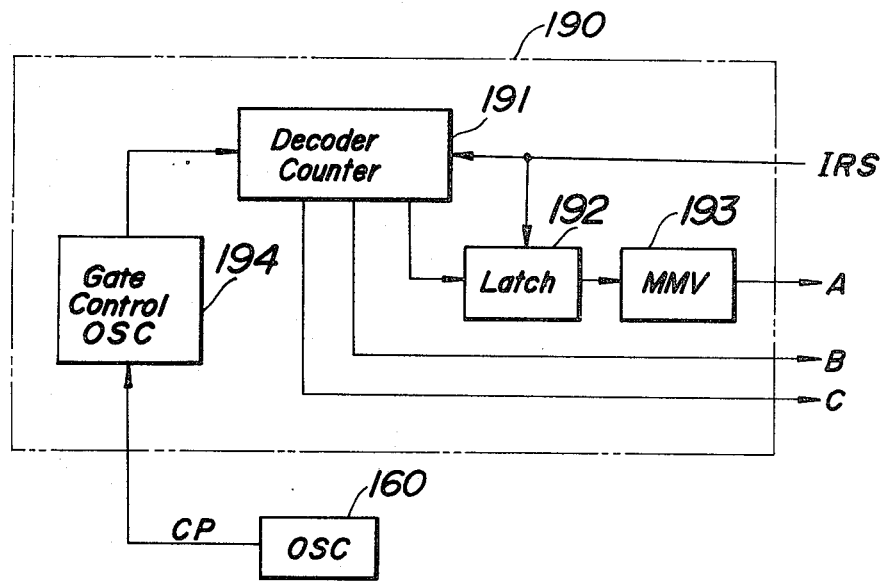
FIG. 6 is a block diagram showing an embodiment of a pulse control circuit shown in FIG. 1.

FIG. 6 illustrates an embodiment of a pulse control circuit 190 including a decoder counter 191, for example, model CD 4022 manufactured by RCA, a latch circuit 192 and a monostable multivibrator 193. The oscillating pulses from the oscillator 160 are applied via a gate control type oscillator 194 to an input terminal of the decoder counter 191 from which pulse trains corresponding to one cycle of the output pulse from the oscillator 194 are produced sequentially. One of those counter decoder output trains is applied to the latch circuit 192 where the pulse of the train is latched. The monostable multivibrator 193 is triggered by the latch output to form a single pulse A shown in FIG. 8 which occurs during recurrence of the oscillating pulses CP of the oscillator 160. A pulse B and a pulse C shown in FIG. 8 can be taken out successively from other output terminals of the decoder counter 191.

Figure 7:
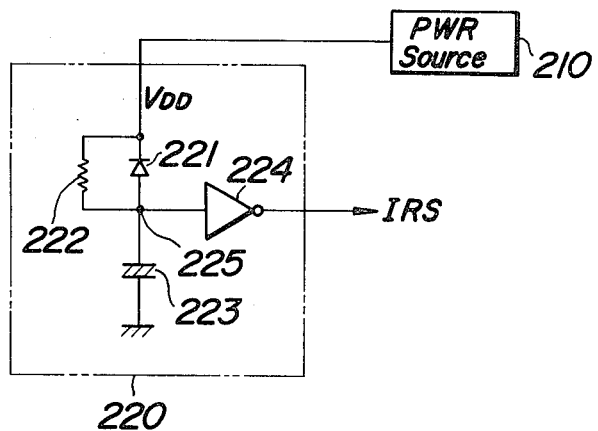
FIG. 7 is a circuit diagram showing an embodiment of an initial reset circuit shown in FIG. 1.

An initial reset circuit 220 may be constructed as shown in FIG. 7, for example. As shown, an output terminal of voltage $V_{DD}$ from the power source circuit 210 is connected to a parallel circuit having a diode 221 and a resistor 222, and a capacitor 223 is connected between the parallel circuit and ground. A terminal 225 of the capacitor 223 on the parallel circuit side is connected to an inverter 224, from which an initial reset signal IRS is produced. Specifically, when the voltage $V_{DD}$ derived from the power source circuit 210 rises, an input voltage to the inverter 224 gradually rises with the time constant of the resistor 222 and the capacitor 234, so that the initial reset signal IRS is derived from the inverter 224, until the input voltage to the inverter 224 exceeds the threshold voltage of the inverter 224.

Figure 8:
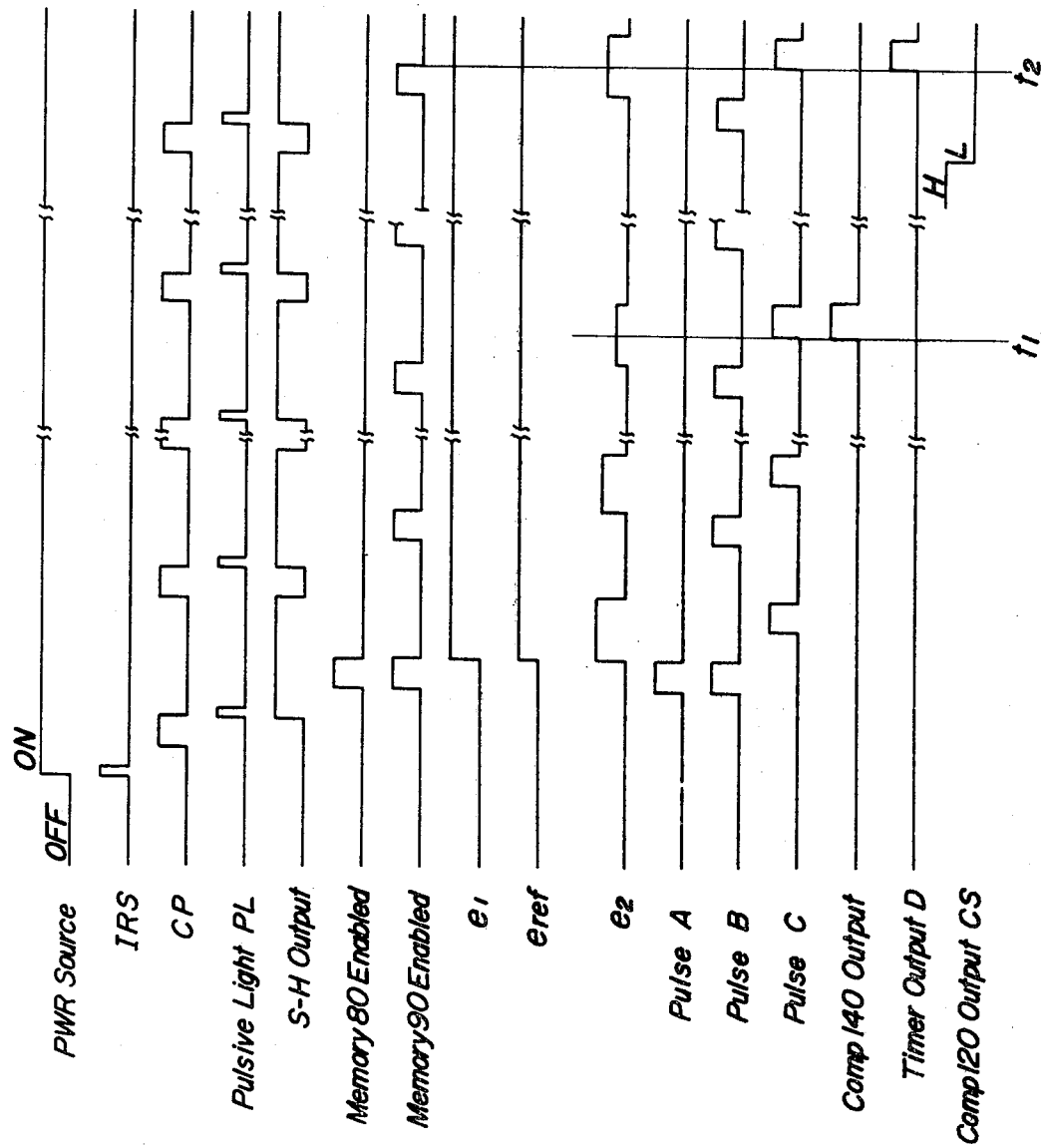
FIG. 8 is a time chart illustrating a set of signal waveforms at the respective portions in the embodiment shown in FIG. 1.

The operations of the embodiment shown in FIG. 1 will be described referring to a timing chart of FIG. 8. When the power source 210 is turned on, the initial reset circuit 220 responds to the output signal from the power source circuit 210 to produce the initial reset signal IRS thereby resetting the first and second memory circuits 80 and 90, and the clock circuit 170. The gain control circuit 180 initially sets the gain of the variable gain amplifier circuit 60 at a predetermined value.

Then, the oscillating circuit 160 starts oscillating and applies the oscillating pulse CP to the light emitting device 10 and the pulse control circuit 190. In this embodiment, the light emitting device 10 emits the pulsive light PL in synchronism with the trailing edge of the oscillating pulse CP. The light emitting device 10 is so designed that the pulsive light PL is emitted by using the discharge current flowing at the time of the discharge of the charge stored in the capacitor 12 which is charged by the oscillating pulse CP, as shown in FIG. 2. The oscillating pulse CP is also supplied to the reset input terminal of the second memory circuit 90 through the OR gate 230. At this time, the second memory circuit 90 is already reset, so that this memory circuit 90 remains in its reset state.

The pulsive light PL from the light emitting device 10 is incident on the light receiving element 30 which produces the photoelectric converted output signal or receiving light signal. This receiving light signal is amplified by the filter amplifier 40 while the external disturbing light or the noise component is removed from the photoelectric converted output signal. The amplifier signal is applied to the peak value holding circuit 50 where the peak value of the amplified signal is held over a period from the trailing edge of one oscillating pulse CP to the leading edge of the next oscillating pulse CP.

The output signal from the peak value holding circuit 50 is applied through the variable gain amplifier circuit 60 having the set initial value to the A/D converter 70 where the peak hold output signal is converted into a digital signal. The digital output signal from the A/D converter 70 is stored as a digital quantity in the first and second memory circuits 80 and 90, respectively, in response to pulse signals A and B produced from the pulse control circuit 190 in synchronism with the trailing edge of the oscillating pulse CP and with a time delay necessary for the A/D conversion. The pulse control circuit 190 produces both of the pulse signals A and B only in the initial stage immediately after the power is turned on and thereafter produces only the signal B. As a result, the first memory circuit 80 holds the initial value of the receiving light signal given through the above-mentioned operation. The output signals from the memory circuits 80 and 90 are converted into analog signals by the D/A converters 100 and 110, respectively. The output signal from the D/A converter 100 is applied to one input terminal of the comparator 141 through the sensitivity setting circuit 130. The output signal from the D/A converter 110 is applied directly to the other input terminal of the comparator 141. In response to these signals applied to the comparator 141, the comparing circuit 140 produces a fire judgement signal at the timing of the pulse signal C from the pulse control circuit 190 applied to the AND gate 142.

In this case, the outputs from the D/A converters 100 and 110 are at the same level, so that $e_{ref} < e_2$ is obtained and the output from the comparator 141 in the comparing circuit 140 is at the L level. Accordingly, even if the pulse signal from the pulse control circuit 190 is applied to the AND gate 142 in the comparing circuit 140, the output from the AND gate 142 remains at the L level and the fire alarm signal generating circuit 150 in the next stage does not operate.

When the oscillating pulse CP of the oscillating circuit 160 rises again, the peak value holding circuit 50 and the second memory circuit 90 are reset, while the first memory circuit 80 is not reset and still holds the initial value of the receiving light signal.

When the oscillating pulse CP of the oscillating circuit 160 falls, the light emitting device 10 produces again the pulsive light PL. The peak value holding circuit 50 detects a peak value of the new receiving light signal. The thus detected peak value is converted into a digital quantity by the A/D converter 70 through the variable gain amplifier circuit 60. By the pulse signal B from the pulse control circuit 190, the newly detected receiving light signal is stored only in the second memory circuit 90 and is again converted into an analog signal by the D/A converter 110 and is subjected to the comparison in the second comparing circuit 140.

Subsequently, similar operations are repeated. For example, as indicated at an instant t1 in FIG. 8, the flow of smoke by an outbreak of fire provides a relation $e_{ref} > e_2$ between the output $e_2$ from the D/A converter 110 and the reference signal $e_{ref}$ from the sensitivity setting circuit 130. At this time, in synchronism with the pulse signal C from the pulse control circuit 190, the comparing circuit 140 produces an H level output to drive the fire alarm signal generating circuit 150.

The clock circuit 170 counts the pulse signal C from the pulse control circuit 190 applied to the second comparing circuit 140. When the clock circuit 170 counts a given number corresponding to 10 hours, for example, the clock circuit 170 produces the pulse signal D to control the gain control circuit 180. At this time, when the output $e_2$ of the D/A converter 110 is lower than the output $e_1$ (initial value) of the D/A converter 100, as indicated at an instant t2 shown in FIG. 8, for example, the output CS of the first comparator 120 is at the L level. Accordingly, the gain control circuit 180 operates in response to the pulse signal D from the clock circuit 170. On the basis of the L level output from the comparator 120 at this time, the gain of the variable gain amplifier circuit 60 is changed and set so that the gain increases by a predetermined number of steps.

While in the above embodiment, the first comparator 120 is provided on the output sides of the D/A converters 100 and 110, a similar effect may be attained by comparing the outputs from the first and second memory circuits 80 and 90 in a digital comparator.

As described above, the photoelectric smoke sensor according to the present invention stores the initial value of the receiving light signal, obtained immediately after power on when the optical system is clean and free from dust and dirt, as a reference value for detecting a fire. At the same time the receiving light signal is stored and refreshed or updated at a given period in another memory circuit. These light receiving light signals are compared with each other for detecting a fire. With respect to the problem that the optical system becomes soiled, if the level of the stored and refreshed receiving light signal falls below the initial value of the receiving light signal thus held, the smoke sensor controls the amplification gain or the attenuation of the receiving light signal to correct the level of the receiving light signal to be approximate to the signal level in the initial stage. When the correcting control has reached the limit, an alarm is issued for maintenance and inspection. With such a construction, even if the optical system becomes soiled progressively and the amount of the received light is decreased, the receiving light signal used for detecting a fire is the same as that obtained when the optical system is clean. Therefore, within a range where the deterioration of the S/N ratio due to the reduction of the receiving light signal caused by dust or dirt on the optical system is allowable, the lack of alarm and the non-fire alarm, i.e., alarm other than fire alarm, are never issued thereby ensuring an extremely stable operation of the smoke sensor. Additionally, the provision of the fail-safe function, in which an alarm is given when the adverse influence by the dust or dirt of the optical system is beyond the ability of compensation by the smoke sensor, enables one to readily know that the smoke sensor needs maintenance and inspection. This ensures reliable control and maintenance of the smoke sensor.

The first embodiment of the smoke sensor according to the invention shown in FIG. 1 has two memory circuits 80 and 90 which store the receiving light signal in the form of digital quantity, respectively. It follows from this that it is necessary to provide two A/D converters separately. The comparison of the present receiving light signal with the stored value is performed in the from of analog signals by converting the stored value to an analog quantity, in order to simplify the constructions of the comparator 120 and the comparing circuit 140. This means that it is necessary to provide the two D/A converters 100 and 110, respectively. This arrangement aids reliable compensation of the receiving light signal, but the circuit construction is less practical because of its complicated arrangement.

Figure 9:
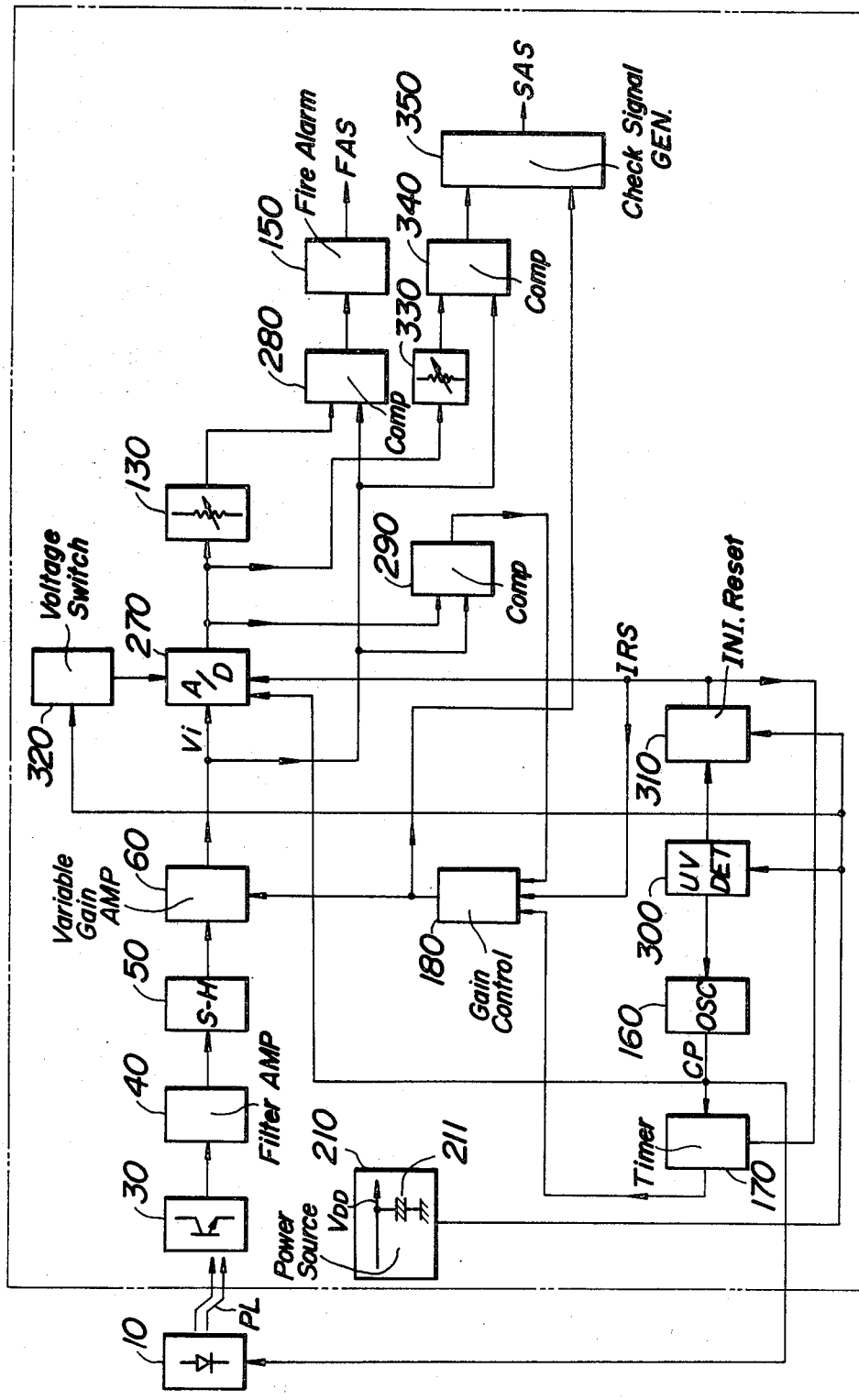
FIG. 9 is a block diagram showing another embodiment of a photoelectric smoke sensor according to the invention.

Another embodiment of the present invention to solve such problems is shown in FIG. 9. In the figure, like symbols are used to designate like portions in FIG. 1.

In FIG. 9, reference numeral 10 designates the light emitting device including a light emitting diode or the like for emitting pulsive light PL at a predetermined period and 20′ designates a light receiving device disposed opposite to and separated from the light emitting device 10 by a given distance, for example, in the order of 100 m at the maximum.

In the light receiving circuit 20′, reference numeral 30 designates the photosensitive element for converting a received light into an electrical signal; 40 designates the filter amplifier which removes the disturbing light and noise component contained in the receiving light signal and amplifies the filtered output; 50 designates the peak value holding circuit which samples the peak value of the receiving light signal and holds the sampled amplitudes; 60 designates the variable gain amplifier circuit operating as a level converting circuit for amplifying with a set gain the receiving light signal from the circuit 50; 270 designates an A/D converting circuit of the sequential comparison type which has the circuit functions of converting the initial value of the receiving light signal into a digital quantity, storing and holding the digital quantity and converting the stored value into an analog quantity to be derived as an output signal.

Figure 10:
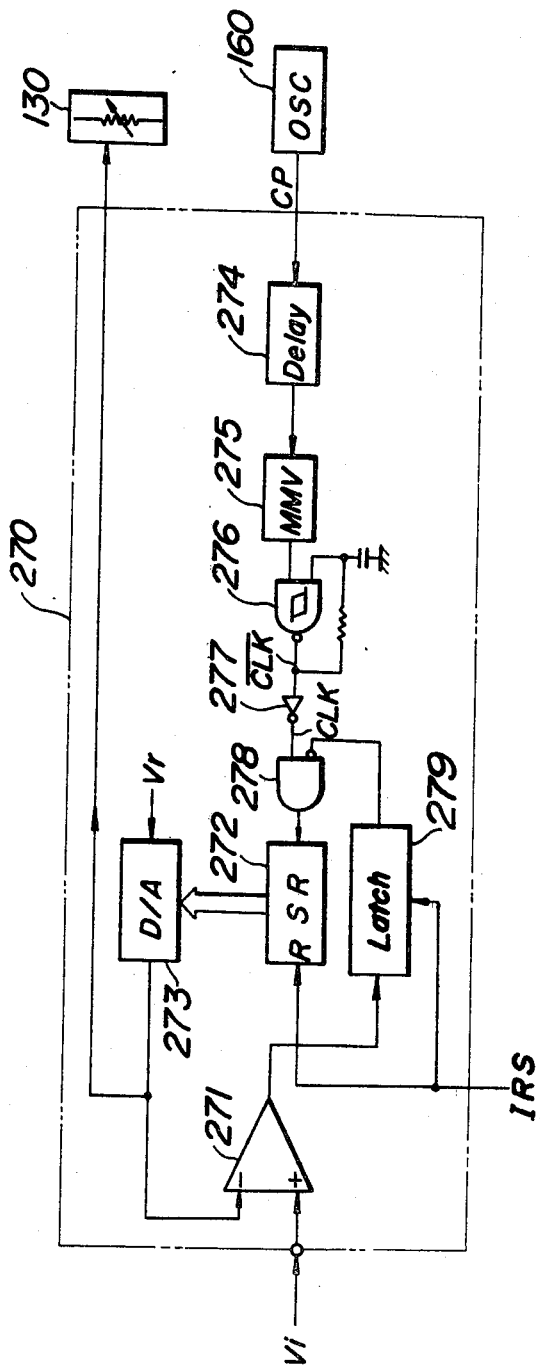
FIG. 10 is a block diagram showing an embodiment of an A/D converting circuit shown in FIG. 9.
Figure 13:
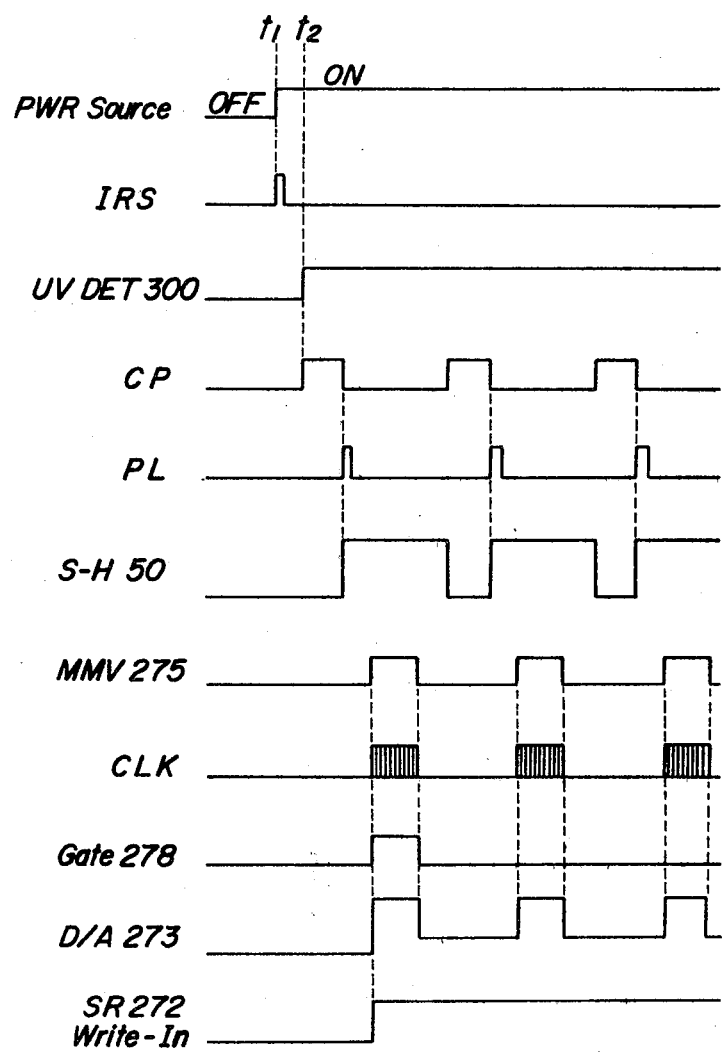
FIG. 13 is a time chart showing a set of signal waveforms at the respective portions in the embodiment shown in FIG. 9.

The A/D converting circuit 270 of this type, which is known to those skilled in the art, may be constructed as shown in FIG. 10. The A/D converting circuit 270 has a conventional comparator 271 for receiving an analog input signal Vi, a shift register 272 for counting a clock pulse CLK until a feedback input to the comparator 271 is coincident with the analog input signal Vi, and a D/A converter 273 for converting the digital quanity in the shift register 272 into an analog quantity depending on a reference voltage Vr and for feeding back the converted signal to the comparator 271. The oscillating pulse CP from the oscillator 160 is applied to a monostable multivibrator 275 through a delay circuit 274 and the output from the monostable multivibrator 275 is supplied to a gate controllable clock generator 276. In this way, a clock pulse $\overline{\text{CLK}}$ is produced only during the occurrence of the output signal from the monostable multivibrator 275, as shown in FIG. 13. A clock pulse CLK, which is an inversion of the pulse $\overline{\text{CLK}}$ by an inverter 277, is applied to an inhibit gate 278. The output from the comparator 271 is supplied to an inhibit input terminal of the inhibit gate 278 via a latch circuit 279. The clock pulse CLK is continuously applied to the shift register 272 until the comparator 271 produces an L level output and the latch circuit 279 operates. Then, the digital value outputted from the shift register 272 is applied to the D/A converter 273. The initial reset signal IRS is applied to a reset input terminal of the shift register 272.

With such a construction, the receiving light signal Vi from the variable gain amplifier circuit 60 is applied to the comparator 271, so that the digital value of the receiving light signal is set in the shift register 272. Under this condition the inhibit gate 278 is interrupted, so that the subsequent clock input CLK in inhibited and thus the content in the shift register 272 is kept approximately at the set value. The output value from the D/A converter 273 is derived as an analog quantity of the initial value held in the shift register 272. The output of the comparator 271 is connected to the inhibit gate 278 via the latch circuit 279. If the comparator 271 produces an L level output, the latch circuit 279 operates and accordingly the clock pulse CLK is not applied to the shift register 272. As a result, the contents in the shift register 272 are kept unchanged.

Again, in FIG. 9, reference numeral 130 designates a sensitivity setting circuit for setting a reference signal level to determine if there is a fire from the initial value of the receiving light signal stored and held in the A/D converting circuit 270. Reference numeral 280 designates a first conventional comparator which compares the receiving light signal from the variable gain amplifier circuit 60 with the reference signal set by the sensitivity setting circuit 130 and produces a comparison output when there is a level difference between these signals. Reference signal 150 designates a fire alarm issuing circuit generating a fire alarm signal when the comparator 280 produces the comparison output.

Besides the fire detecting system as mentioned above, explanation will be given about a system for compensating for the attenuation of the receiving light signal due to the dust and dirt or soil on the optical system. A second conventional comparator 290 compares the output signal from the variable gain amplifier circuit 60 with the initial value output from the A/D converting circuit 270 of the sequential comparison type and produces an output signal when there is a level difference between these outputs. The clock circuit 170 counts the output signal from the oscillator circuit 160 to provide the pulse signal determining the gain correction timing of the variable amplifier circuit 60 at a fixed period, for example, at every 10 hours. The gain control circuit 180 operates as a level correcting circuit for correcting the set gain of the variable gain amplifier circuit 60 by applying the pulse signal from the clock circuit 170 so as to compensate for an amount of the light attenuation. The power source circuit 210 supplies electric power of a voltage $V_{DD}$ to the respective circuits through a capacitor 211 having a large capacitance. Reference numeral 300 designates an under-voltage detecting circuit for detecting an under-voltage of the power source voltage $V_{DD}$. An initial reset circuit 310 responds to the output signal from the under-voltage detecting circuit 300 to apply the initial reset signal IRS to the sequential comparison type A/D converting circuit 270, the gain control circuit 180 and the clock circuit 170 for the purpose of the initialization of the respective circuits.

Figure 11:
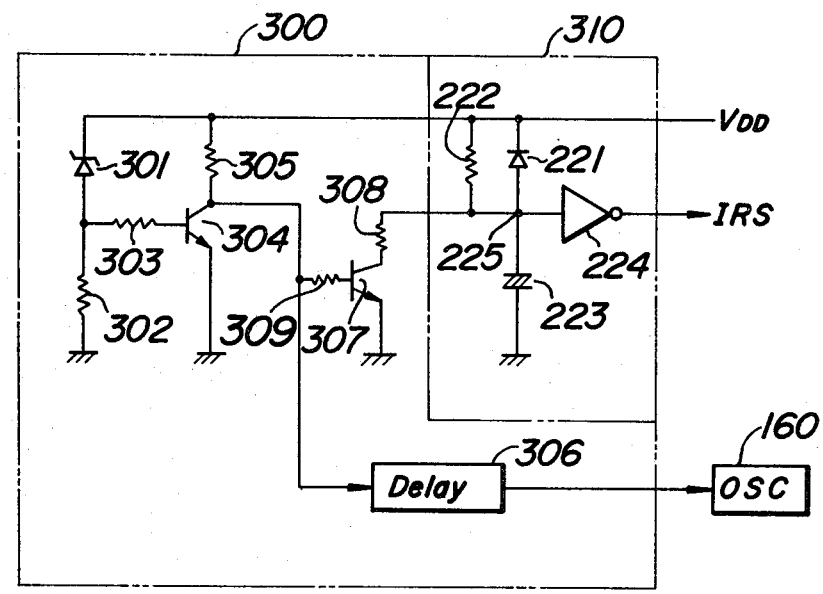
FIG. 11 is a circuit diagram showing embodiments of an initial reset circuit and an under-voltage detecting circuit shown in FIG. 9.

As shown in FIG. 11, the initial reset circuit 310 has a circuit arrangement substantially the same as that of the initial reset circuit 220 shown in FIG. 7. Supplied to the connection point 225 is the under-voltage detecting signal from the under-voltage detecting circuit 300. The under-voltage detecting circuit 300 has a series circuit having a Zener diode 301 and a resistor 302, across which circuit the power source voltage $V_{DD}$ is applied. The connection point therebetween is connected to the base of a transistor 304, through a resistor 303. The transistor 304 is connected at the emitter to ground and at the collector to the power source voltage $V_{DD}$ through a resistor 305. When the power source voltage $V_{DD}$ decreases, the anode side voltage of the Zener diode 301 reduces and the transistor 304 is turned off. Accordingly, the collector thereof provides the under-voltage detecting signal of H level. This H level signal is applied to the oscillator 160 through a delay circuit 306. As shown in FIG. 13, at an instant t2 that a given time has lapsed after the power is turned on, the oscillator 160 starts oscillating. The collector output from the transistor 304 is applied to the base of a transistor 307 via a resistor 309. The collector of the transistor 307 is connected to the inverter 224 through a resistor 308 and the connection point 225. The emitter of the transistor 307 is grounded.

A voltage switching circuit 320 shown in FIG. 9 controls the voltage supply to the sequential comparison type A/D converting circuit 270. In operation, only when the pulse signal CP is applied to the A/D converting circuit 270, that is, only when the A/D converting circuit 270 produces an analog quantity, does the voltage switching circuit 320 apply a pulsive voltage of 12 V, for example, as a standard power supply voltage, to the A/D converting circuit 270. In other cases, the supply voltage from the circuit 320 is switched to a lower voltage, for example, to such an extent so as not to fail to change or erase the contents in the register 272 of the A/D converting circuit 270, in FIG. 10, thereby reducing the power consumption in the A/D converter 270. In the case of a short time interruption of power supply, the stored initial value is prevented from being erased by the power supply from the large capacitive capacitor 211 provided in the power source circuit 210.

Figure 12:
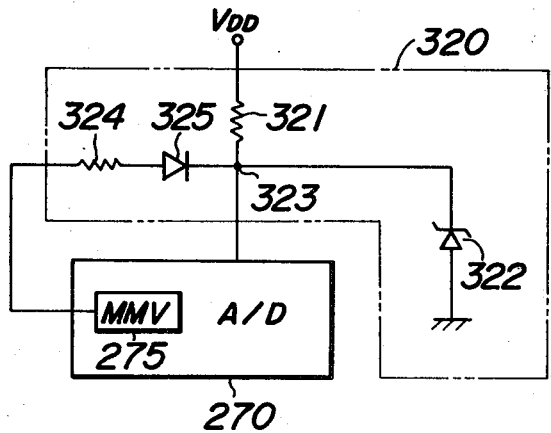
FIG. 12 is a circuit diagram showing an embodiment of a power source switching circuit shown in FIG. 9.

FIG. 12 is an embodiment of the voltage source switching circuit 320. The power source voltage $V_{DD}$ is applied via a resistor 321 to the cathode of a Zener diode 322, the anode of which is grounded. A connection point 323 between the Zener diode 322 and the resistor 321 is connected to a power source terminal of the A/D converter 270. The output terminal of the monostable multivibrator 275 in the A/D converter 270 is connected to the point 323, through a resistor 324 and a diode 325. When the resistor 321 is 100 KΩ, the resistor 324 is 1 KΩ, and a constant voltage of the Zener diode 322 is 6 V, a normal Zener current flows into the Zener diode 322 via the resistor 321, so that the constant voltage 6 V by the Zener diode 322 is applied to the A/D converter 270 only when the output voltage from the monostable multivibrator 275 is at the H level (=12 V). When the output of the monostable multivibrator 275 is at the L level (0 V), a voltage, for example, 3 V obtained by dividing the voltage $V_{DD}$ by the high resistance resistor 321 and the Zener diode 322 is applied to the A/D converter 270.

In the embodiment shown in FIG. 9, there is further provided means for detecting an abnormal state and issuing an alarm when an optical path between the light emitting device 10 and the light receiving means 20' is physically interrupted, which is a problem peculiar to a smoke sensor of the separation type. This means includes an attenuation circuit 330, for example, a variable resistor, for producing a signal attenuated by a given amount, for example, by 90%, of the output signal from the sequential comparison type A/D converting circuit 270, a conventional comparing circuit 340 for producing an output when the output from the variable gain amplifier circuit 60 is reduced lower than the signal level of the attenuator circuit 330, and an inspection signal generating circuit 350 for producing an inspection signal indicating the interruption of the optical path in response to the output signal from the comparing circuit 340 in order to urge an inspection of the smoke sensor. The inspection signal generating circuit 350 also produces the inspection signal in response to a signal produced from the variable gain control circuit 180 when it is not possible to adjust the gain of the variable gain amplifier circuit 60 after the gain control has reached the limit. Accordingly, the inspection signal generating circuit 350 includes an OR gate to which the outputs from the comparing circuit 340 and the gain control circuit 180 are applied, and an amplifier for amplifying the output from the OR gate.

The variable gain amplifier shown in FIG. 4 which is employed as the level converting means 60 of the light receiving signal in the above-mentioned embodiment, may be replaced by a variable attenuator having the resistor voltage dividing circuit shown in FIG. 5. In this case, a circuit for controlling the attenuation rate is used as the converting level correcting circuit 180 in place of the gain control circuit.

The operation of the smoke sensor shown in FIG. 9 will be described.

The storing and holding of the initial value immediately after the power is turned on will be first explained referring to the timing charts illustrated in FIG. 13. It is assumed that the power source is turned on at an instant t1. When the power is turned on, the power source circuit 210 supplies electric power to the respective circuits. The power supply is detected by the under-voltage detecting circuit 300. Then, the reset circuit 310 produces an initial reset signal IRS which clears the contents of the shift register 272 (see FIG. 10) in the A/D converting circuit 270 of the sequential comparison type, sets the gain control circuit 180 at the initial gain set control state, and resets the clock circuit 170.

Then, the output from the under-voltage detecting circuit 300 triggers the oscillating circuit 160 to generate the pulse signal CP at a given period which is applied to the light emitting device 10. The pulsive light PL is emitted in synchronism with the trailing edge of the oscillating pulse CP. The light pulse PL is received by the light receiving element 30 where the light pulse PL is converted into the electrical signal or the light receiving signal. The converted electrical signal is amplified by the filter amplifier 40 and the peak value of the amplified signal is held by the peak value holding circuit 50. Then, the peak hold value is level-converted by the variable gain amplifier circuit 60 and in turn is sequentially supplied to the A/D converting circuit 270 of the sequential comparison type.

As shown in FIG. 10, the A/D converting circuit 270 receives the clock signal CLK. The clock signal CLK is applied through the gate 278 to the shift register 272 at a given timing to start the counting of the shift register 272 and the counting output is converted into an analog signal by the D/A converter 273. At this time, the counting operation by the shift register 272 continues until the analog signal is coincident with the light receiving signal applied to the comparator 271. When the analog signal and the light receiving signal are coincident with each other, the inhibit gate 278 is disabled by the output from the comparator 271 thereby inhibiting the subsequent supply of the clock signal CLK. As a result, the initial value of the light receiving signal is stored and held in the shift register 272 and the initial value thus held is converted into the analog signal by the D/A converter 273. This analog signal is outputted from the A/D converting circuit 270.

When the smoke of a fire flows into the space between the light emitting device 10 and the light receiving device 20' due to the outbreak of a fire, the light receiving signal reduces its level in accordance with the amount of the light attenuation caused by the smoke of the fire. When the receiving light signal is below the reference level set by the sensitivity setting circuit 130, the alarm issuing circuit 150 is operated by the output from the comparator 280 to produce the alarm issuing signal, which is used to issue a fire alarm. When the dust and soil accumulate on the optical system through a long time use, there is a level difference between the present receiving light signal and the initial value, so that the comparator 290 produces its output signal. In synchronism with the pulse signal outputted from the clock circuit 170 at a given period, e.g. at every 10 hours, the gain control circuit 180 changes the gain of the variable gain amplifier circuit 60 by 1% in terms of the light attenuation rate of the smoke at every 10 hours. In this way, even if the dust or the like has accumulated on the optical system, the receiving light signal obtained through the variable gain amplifier circuit 60 has the same level as that in the initial stage even after several tens hours. Additionally, a rate of gain change of the variable gain amplifier circuit 60 is extremely smaller than a rate of reduction of the receiving light signal due to the smoke of a fire. Therefore, the gain change is scarcely influenced upon detecting a fire. This fact eliminates the necessity of inspection and cleaning of the smoke sensor for a long period and ensures a stable fire supervising operation.

Further, when an obstacle is placed in a location to interrupt the optical path between the light emitting device 10 and the light receiving device 20', the comparator 340 detects an abrupt reduction in the amount of light to produce an output signal which drives the inspection signal generating circuit 350 to issue an alarm. As a consequence, the smoke sensor is surely prevented from being placed in an improper supervising state.

As described above, in the embodiment shown in FIG. 9, the means which digitally stores and holds the receiving light signal, which is obtained at the initial stage of the smoke sensing operation, as a reference signal for judging a fire as well as correcting the reduction of the amount of light due to causes other than the fire, and which converts the stored signal into an analog quantity, is comprised of a digital memory section 272 and the D/A converting section 273 in the A/D converter circuit 270 of the sequential comparison type. Therefore, the present invention extremely simplifies the circuit construction for converting an analog quantity to a digital quantity which is stored and held and for producing an output after the stored digital signal is converted into the analog quantity again. As a result, the smoke sensor of the present invention is practical in use, high in reliability and low in cost.

Moreover, the light attenuation due to dust, dirt or the like which has accumulated on the optical system is corrected by the circuit technology to ensure stable fire supervision for a long time. Even when a short time interruption of the power supply occurs, the initial value of the receiving light signal is not erased and kept unchanged. When the optical path is physically interrupted, an alarm is issued for demanding the inspection of the sensor. In this respect, the reliability of the sensor is further improved.

What is claimed is:

1. A photoelectric smoke sensor for producing a fire alarm signal in response to light generated by a light emitting device and received by a light receiving device spaced from the light emitting device, the fire alarm signal being generated when an amount of attenuation of the received light exceeds a predetermined level due to smoke flowing into the space between the light emitting device and the light receiving device, the light receiving device producing a receiving light signal, having a level, in response to the received light, said photoelectric smoke sensor comprising:

a signal level converting circuit for varying the level of the receiving light signal produced by the light receiving device in response to a converting level control signal to produce a converted level receiving light signal;

a memory circuit, coupled to said signal level converting circuit, for storing and holding in digital form an initial value of the converted level receiving light signal;

a D/A converting circuit, coupled to said memory circuit, for converting the digital form of the initial value of the converted level receiving light signal into an analog output signal;

a first comparing circuit, coupled to said D/A converting circuit and said signal level converting circuit, for comparing the analog output signal with the converted level receiving light signal to produce the fire alarm signal when there is a level difference between the analog output signal and the converted level receiving light signal;

a second comparing circuit, coupled to said D/A converting circuit and said signal level converting circuit, for comparing the analog output signal with the converted level receiving light signal at a predetermined period and for producing a comparison output signal when there is a level difference between the analog output signal and the converted level receiving light signal; and a converting level correcting circuit, coupled to said second comparing circuit, for producing the converting level control signal in response to the comparison output signal.

2. A photoelectric smoke sensor as claimed in claim 1, further comprising means, coupled to said converting level correcting circuit, for producing an alarm signal for maintenance and inspection when the converting level control signal reaches a limit.

3. A photoelectric smoke sensor as claimed in claim 1, wherein said signal level converting circuit includes a variable gain amplifier for receiving the receiving light signal, the gain of said variable gain amplifier being varied by the converting level control signal.

4. A photoelectric smoke sensor as claimed in claim 1, wherein said signal level converting circuit includes a variable attenuator for attenuating the receiving light signal and controllable analog switches for varying said variable attenuator, said analog switches being controlled in response to the converting level control signal.

5. A photoelectric smoke sensor for producing a fire alarm signal in response to light generated by a light emitting device and received by a light receiving device spaced from the light emitting device, the fire alarm signal being generated when an amount of attenuation of the received light exceeds a predetermined level due to smoke flowing into the space between the light emitting device and the light receiving device, the light receiving device producing a receiving light signal, having a level, in response to the received light, said photoelectric smoke sensor comprising:

a signal level converting circuit for varying the level of the receiving light signal produced by the light receiving device in response to a converting level control signal to produce a converted level receiving light signal;

a first memory circuit, coupled to said signal level converting circuit, for storing an initial value of the converted level receiving light signal;

a second memory circuit, coupled to said signal level converting circuit, for storing periodically the converted level receiving light signal at a first predetermined period;

a comparing circuit, coupled to said first memory circuit and said second memory circuit, for comparing the stored initial value of the converted level receiving light signal with the periodically stored converted level receiving light signal to produce a comparison output signal when there is a level difference between the stored initial value of the converted level receiving light signal and the periodically stored converted level receiving light signal;

a converting level correcting circuit, coupled to said comparing circuit, for producing the converting level control signal in response to the comparison output signal; and a clock circuit for generating a clock signal, said converting level correcting circuit being controlled in response to the clock signal to produce a corrected converting level control signal at a second predetermined period longer than the first predetermined period.

6. A photoelectric smoke sensor as claimed in claim 5, further comprising means, coupled to said converting level correcting circuit, for producing an alarm signal for maintenance and inspection when the converting level control signal reaches a limit.

7. A photoelectric smoke sensor as claimed in claim 5, wherein said signal level converting circuit includes a variable gain amplifier for receiving the receiving light signal, the gain of said variable gain amplifier being varied by the converting level control signal.

8. A photoelectric smoke sensor as claimed in claim 5, wherein said signal level converting circuit includes a variable attenuator for attenuating the receiving light signal and controllable analog switches for varying said variable attenuator, said analog switches being controlled in response to the converting level control signal.

* * * * *

UNITED STATES PATENT AND TRADEMARK OFFICE
CERTIFICATE OF CORRECTION

PATENT NO. : 4,317,113
DATED : February 23, 1982
INVENTOR(S) : Hiroshi Honma

It is certified that error appears in the above—identified patent and that said Letters Patent is hereby corrected as shown below:

Column 3, line 33, "futher" should be "further".

Column 5, line 55, after "190" insert --designates--.

Column 6, line 6, "IRs" should be "IRS".

Column 9, line 49, "fier" should be "fied".

Column 11, line 10, after "These" delete "light".

Column 11, line 46, "from" should be "form".

Signed and Sealed this

Twenty-first Day of September 1982

[SEAL]

Attest:

*Attesting Officer*

GERALD J. MOSSINGHOFF

*Commissioner of Patents and Trademarks*